United States Patent [19]

Alban et al.

[11] Patent Number: 5,420,118

[45] Date of Patent: * May 30, 1995

[54] GEL TYPE COSMETIC COMPOSITIONS

[75] Inventors: Noelle C. Alban, Naugatuck; George E. Deckner, Trumbull, both of Conn.

[73] Assignee: Richardson-Vicks Inc., Shelton, Conn.

[*] Notice: The portion of the term of this patent subsequent to Dec. 17, 2008 has been disclaimed.

[21] Appl. No.: 68,564

[22] Filed: May 27, 1993

Related U.S. Application Data

[63] Continuation of Ser. No. 621,161, Nov. 30, 1990, abandoned.

[51] Int. Cl.$^6$ ............................................. A61K 31/695
[52] U.S. Cl. ........................................ 514/63; 514/772; 514/772.5; 514/772.6; 514/781; 514/847; 514/738
[58] Field of Search .................. 514/781, 786, 847, 63

[56] References Cited

U.S. PATENT DOCUMENTS

| | | | |
|---|---|---|---|
| Re. 29,814 | 10/1978 | Snyder | 424/81 |
| 4,421,769 | 12/1983 | Dixon et al. | 424/358 |
| 4,515,784 | 5/1985 | Bogardus et al. | 514/63 |
| 4,529,588 | 7/1985 | Smith et al. | 424/70 |
| 4,534,964 | 8/1985 | Herstein et al. | 424/70 |
| 4,728,457 | 3/1988 | Fieler et al. | 252/174.15 |
| 4,741,855 | 5/1988 | Grote et al. | 252/142 |
| 4,859,456 | 8/1989 | Marschner | 424/47 |
| 4,863,725 | 9/1989 | Deckner et al. | 424/81 |
| 4,954,532 | 9/1990 | Elliot et al. | 514/846 |
| 4,960,764 | 10/1990 | Figueroa et al. | 514/63 |
| 4,973,473 | 11/1990 | Schneider et al. | 424/63 |
| 4,978,526 | 12/1990 | Gesslein et al. | 424/70 |
| 5,073,371 | 12/1991 | Turner et al. | 424/401 |
| 5,073,372 | 12/1991 | Turner et al. | 424/401 |

FOREIGN PATENT DOCUMENTS

| | | | |
|---|---|---|---|
| 107118 | 5/1984 | European Pat. Off. | A61K 7/08 |
| 89-250461/35 | 8/1989 | European Pat. Off. | A61K 7/48 |
| 330369 | 8/1989 | European Pat. Off. | A61K 7/48 |
| 64-288836/40 | 8/1989 | Japan | A61K 7/06 |
| 1211518 | 8/1989 | Japan | A61K 7/06 |
| 64-336071/46 | 10/1989 | Japan | A61K 7/00 |
| 1250305 | 10/1989 | Japan | A61K 7/00 |
| 2192194 | 1/1988 | United Kingdom | A61K 7/07 |
| 88-002224/01 | 6/1990 | United Kingdom | A61K 7/07 |

OTHER PUBLICATIONS

Remington's Pharmaceutical Sciences 15th Ed. Mack Pub Co., Easton, Pa., 1975.

*Primary Examiner*—Marianne M. Cintins
*Assistant Examiner*—M. Moezie
*Attorney, Agent, or Firm*—David K. Dabbiere; Anthony D. Sabatelli; Leonard W. Lewis

[57] ABSTRACT

A skin care composition in the form of a substantially oil-free aqueous gel comprising a water-soluble humectant, a hydrophilic gelling agent and a specific silicone component. The compositions provide improved skin feel and residue characteristics together with excellent moisturizing, emolliency, rub-in and absorption characteristics.

16 Claims, No Drawings

GEL TYPE COSMETIC COMPOSITIONS

This is a continuation of application Ser. No. 07/621,161, filed on Nov. 30, 1990, now abandoned.

TECHNICAL FIELD

The present invention relates to facial-care cosmetic compositions. In particular it relates to cosmetic compositions in the form of substantially oil-free aqueous gels which provide improved skin feel and residue characteristics together with excellent moisturizing, emolliency, rub-in and absorption characteristics.

BACKGROUND OF THE INVENTION

The treatment of human skin with various agents has been undertaken for many years with the goal being to keep the skin in a smooth and supple condition. Skin has the tendency to dry out when exposed to conditions of low humidity or to detergent solutions for extended periods. Skin is made up of several layers of cells which coat and protect the keratin and collagen fibrous proteins that form the skeleton of its structure. The outermost of these layer, referred to as the stratum corneum, is known to be composed of 250 A protein bundles surrounded by 80 A thick layers. Anionic surfactants and organic solvents typically penetrate the stratum corneum membrane and, by delipidization (i.e. removal of the lipids from the stratum corneum), destroy its integrity. This destruction of the skin surface topography leads to a rough feel and may eventually permit the surfactant or solvent to interact with the keratin, creating irritation.

It is now recognized that maintaining the proper water gradient across the stratum corneum is important to its functionality. Most of this water, which is sometimes considered to be the stratum corneum's plasticizer, comes from inside the body. If the humidity is too low, such as in a cold climate, insufficient water remains in the outer layers of the stratum corneum to properly plasticize the tissue; and the skin begins to scale and becomes itchy. Skin permeability is also decreased somewhat when there is inadequate water across the stratum corneum. On the other hand, too much water on the outside of the skin causes the stratum corneum to ultimately absorb three to five times its own weight of bound water. This swells and puckers the skin and results in approximately a two to three fold increase in the permeability of the skin to water and other polar molecules.

Thus, a need exists for compositions which will assist the facial stratum corneum in maintaining the optimum performance of its barrier and water retention functions, in spite of deleterious interactions which the skin may encounter in washing, work, and recreation.

Conventional cosmetic cream and lotion compositions as described, for example, in Sagarin, *Cosmetics Science and Technology*, 2nd Edition, Volume 1, Wiley Interscience (1972) and *Encyclopedia of Chemical Technology*, Third Edition, Volume 7 are known to provide varying degrees of emolliency, barrier and water-retention (moisturizing) benefits. However, they can also suffer serious negatives in terms of skin feel (i.e. they often feel very greasy on the skin) as well as having poor rub-in, absorption and residue characteristics. Other cosmetic compositions are disclosed in, for example, U.S. Pat. No. 4,837,019 to Georgalas et al., issued Jun. 16, 1989 and also in U.S. Pat. No. 4,863,725 to Deckner et al., issued Sep. 5, 1989, both of which are incorporated by reference herein.

To improve moisturizing benefits water-soluble humectants such as glycerine have been added to cosmetic compositions; however these water-soluble humectants generally significantly increase the tacky feeling. Applicants have found that the use of a specific silicone component in substantially oil-free aqueous gel-type compositions provides significantly improved skin feel and provides a visually appealing product. Further, these compositions, when applied to the skin, provide the user with improved make-up application and protection from environmental factors (e.g., irritants such as wind, heat and cold) as well as protection from common household irritants (e.g., cleansers and the like). These substantially oil-free gel-type cosmetic compositions are also particularly useful in warmer climates because they reduce the tack associated with heat and humidity.

The present invention therefore provides substantially oil-free gel-type cosmetic compositions which provide improvements in absorption, residue and skin-feel characteristics without detriment to either short or longer term moisturizing effectiveness or emolliency.

It is therefore an object of the present invention to provide improved facial compositions which provide reduced tack and provide the user with a smoother skin feel. It is a further object of the present invention to provide oil-free moisturization to minimize skin regreasing over time. It is still a further object to provide skin care compositions which, when applied, provide improved make-up application as well as improved protection from environmental and common household irritants.

These and other objects of this invention will become apparent in light of the following disclosure.

SUMMARY OF THE INVENTION

Accordingly, the present invention provides a skin care composition in the form of a substantially oil-free aqueous gel comprising:
(a) from 0.5% to 20% by weight of a water-soluble humectant;
(b) from 0.1% to 20% by weight of a hydrophilic gelling agent; and
(c) from 1.0% to 10% by weight of a silicone component consisting essentially of
  i) a silicone gum having a molecular weight of from about 200,000 to about 540,000 selected from the group consisting of dimethiconol, fluorosilicone and dimethicones or mixtures thereof; and
  ii) a silicone-based carrier having a viscosity from about 5 cps. to about 100 cps.
  wherein the ratio of i) to ii) is from about 10:90 to about 20:80, preferably from about 13:87 to about 17:83, and wherein said component has a final viscosity of from about 500 cps. to about 10,000 cps. preferably from about 1,000 cps. to about 5,000 cps.

All percentages and ratios used herein are by weight and all measurements at 25° C. unless otherwise indicated.

DETAILED DESCRIPTION OF THE INVENTION

The compositions of the present invention contain three essential ingredients as well as various optional components as indicated below. All levels and ratios are by weight of total composition, unless otherwise indicated.

Water-soluble Humectant

A first essential ingredient is a water-soluble humectant. Most preferred for use herein is glycerine (sometimes know as glycerol or glycerin) and derivatives thereof (e.g., propoxylated glycerine and ethoxylated glycerine). Chemically, glycerine is 1,2,3-propanetriol and is a product of commerce. One large source of the material is as a byproduct in the manufacture of soap. Other useful humectants include D-panthenol, hyaluronic acid, glucosides (e.g., Glucam E10 and E20 available from Amerchol Corporation), lactamide monoethanolamine, and acetamide monoethanolamine.

Mixtures of these water-soluble humectants can also be used.

In the present invention the water-soluble humectant, is present at a level of from about 0.5% to about 20%, preferably from about 1% to about 10%, more preferably from about 4% to about 8% by weight of the composition.

Hydrophilic Gelling Agent

The compositions of the present invention also contain a hydrophilic gelling agent at a level preferably from about 0.1% to about 20%, more preferably from about 0.2% to about 2%, and most preferably from about 0.3% to about 1%. The gelling agent preferably has a neutralized viscosity (1% aqueous solution, 20° C., Brookfield RVT) of at least about 4000 cps, more preferably at least about 10,000 cps, and most preferably at least about 50,000.

Suitable hydrophilic gelling agents can generally be described as water-soluble or colloidally water-soluble polymers, and include cellulose ethers (e.g. hydroxyethyl cellulose, methyl cellulose, hydroxy propylmethyl cellulose), polyvinylpyrrolidone, polyvinylalcohol, guar gum, hydroxypropyl guar gum and xanthan gum.

Preferred for use in the compositions of the present invention are carboxylic acid copolymers. These copolymers consist essentially of a colloidally water-soluble polymer of acrylic acid crosslinked with a polyalkenyl polyether of a polyhydric alcohol, and optionally an acrylate ester or a polyfunctional vinylidene monomer.

Preferred copolymers useful in the present invention are polymers of a monomeric mixture containing 95.9 to 98.8 weight percent of an olefinically unsaturated carboxylic monomer selected from the group consisting of acrylic, methacrylic and ethacrylic acids; about 1 to about 3.5 weight percent of an acrylate ester of the formula:

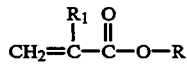

wherein R is an alkyl radical containing 10 to 30 carbon atoms and $R_1$ is hydrogen, methyl or ethyl; and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97,9 weight percent of acrylic acid and from about 2.5 to about 3.5 weight percent of acrylic esters wherein the alkyl group contains 12 to 22 carbon atoms, and $R_1$ is methyl, most preferably the acrylate ester is stearyl methacrylate. Preferably, the amount of crosslinking polyalkenyl polyether monomer is from about 0.2 to 0.4 weight percent. The preferred crosslinking polyalkenyl polyether monomers are allyl pentaerythritol, trimethylolpropane diallylether or allyl sucrose. These polymers are fully described in U.S. Pat. No. 4,509,949, to Huang et al., issued Apr. 5, 1985, this patent being incorporated herein by reference.

Other preferred copolymers useful in the present invention are the polymers which contain at least two monomeric ingredients, one being a monomeric olefinically-unsaturated carboxylic acid, and the other being a polyalkenyl, polyether of a polyhydric alcohol. Additional monomeric materials may be present in the monomeric mixture if desired, even in predominant proportion.

The first monomeric ingredient useful in the production of these carboxylic polymers are the olefinically-unsaturated carboxylic acids containing at least one activated carbon-to-carbon olefinic double bond, and at least one carboxyl group. The preferred carboxylic monomers are the acrylic acids having the general structure

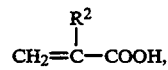

wherein $R^2$ is a substituent selected from the class consisting of hydrogen, halogen, and the cyanogen (—C≡N) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent of the total monomers used. More preferably the range will be from about 96 to about 97.9 weight percent.

The second monomeric ingredient useful in the production of these carboxylic polymers are the polyalkenyl polyethers having more than one alkenyl ether grouping per molecule. The most useful possess alkenyl groups in which an olefinic double bond is present attached to a terminal methylene grouping, $CH_2=C<$.

The additional monomeric materials which may be present in the polymers include polyfunctional vinylidene monomers containing at least two terminal $CH_2<$ groups, including for example, butadiene, isoprene, divinyl benzene, divinyl naphthlene, allyl acrylates, and the like. These polymers are fully described in U.S. Pat. No. 2,798,053, to Brown, H. P., issued Jul. 2, 1957, this patent being incorporated herein by reference.

Examples of carboxylic acid copolymers useful in the present invention include Carbomer 934, Carbomer 941, Carbomer 950, Carbomer 951, Carbomer 954, Carbomer 980, Carbomer 981, Carbomer 1342, acrylates/C10-30 alkyl acrylate cross polymer (available as Carbopol 934, Carbopol 941, Carbopoly 950, Carbopol 951, Carbopol 954, Carbopol 980, Carbopol 981, Carbopol 1342, and the Pemulen series, respectively, from B. F. Goodrich).

Other carboxylic acid copolymers useful in the present invention include sodium salts of acrylic acid/acrylamide copolymers sold by the Hoechst Celanese Corporation under the trademark of Hostaceren PN73.

Also included are the hydrogel polymers sold by lipo Chemicals Inc. under the trademark of HYPAN hydrogels. These hydrogels consist of crystalline plicks of nitrites on a C—C backbone with various other pendant groups such as carboxyls, amides, and amidines. An example would include HYPAN SA100 H, a polymer powder available from Lipo Chemical.

Neutralizing agents suitable for use in neutralizing acidic group containing copolymers herein include sodium hydroxide, potassium hydroxide, ammonium hydroxide, monoethanolamine, diethanolamine, triethanolamine, tetrahydroxypropyl ethylenediamine (available as the Quadrol$^R$ series from BASF), tris, arginine, triisopropylamine and lysine.

The carboxylic acid copolymers can be used individually or as a mixture of two or more polymers and comprise from about 0.025 to about 0.75, preferably from about 0.05 to about 0.25 and most preferably from about 0.075 to about 0.175 percent of the compositions of the present invention.

For the present invention the weight ratio of carboxylic acid copolymer to cationic surfactant is preferably from about 1:10 to about 10: 1.

Neutralizing agents suitable for use in neutralizing acidic group containing hydrophilic gelling agents herein include sodium hydroxide, potassium hydroxide, ammonium hydroxide, monoethanolamine, diethanoiamine, triethanolamine, tetrahydroxypropyl ethylenediamine (available as the Quadrol ® series from BASF), tris, arginine, triisopropylamine and lysine.

Silicone Component

The present invention comprises from 1.0% to 10% by weight of a silicone component consisting essentially of i) a silicone gum having a molecular weight of from about 200,000 to about 540,000 selected from the group consisting of dimethiconol, fluorosilicone and dimethicones or mixtures thereof; and ii) a silicone-based carrier having a viscosity from about 0.65 cps. to about 100 cps. and wherein the ratio of i) to ii) is from about 10:90 to about 20:80, preferably from about 13:87 to about 17:83, and wherein said component has a final viscosity of from about 500 cps. to about 10,000 cps. preferably from about 1,000 cps. to about 5,000 cps.

The dimethiconol component of the present invention has the chemical structure of

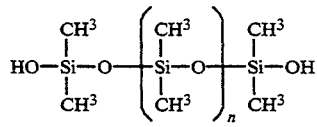

where n is from about 2700 to about 4500, preferably from about 3200 to about 4300 and most preferably n is from about 4000 to about 4300. The dimethiconol component has a molecular weight of from about 200,000 to about 300,000, preferably from about 240,000 to about 260,000 and most preferably about 250,000.

The fluorosilicones useful in the present invention have a molecular weight of from about 200,000 to about 300,000, preferably from about 240,000 to about 260,000 and most preferably about 250,000.

The dimethicones of the present invention are silicone gums. These silicone gums are described by Petrarch and others including U.S. Pat. No., 4,152,416, May 1, 1979 to Spitzer, et al. and Noll, Walter, *Chemistry and Technology of Silicones,* New York: Academic Press 1968. Also describing silicone gums are General Electric Silicone Rubber Product Data Sheets SE 30, SE 33, SE 54 and SE 76. All of these described references are incorporated herein by reference. "Silicone gum" materials useful herein denote high molecular weight materials having a molecular weight of from about 200,000 to about 600,000. Specific examples include polydimethylsiloxane, (polydimethylsiloxane) (methylvinylsiloxane) copolymer, poly(dimethylsiloxane) (diphenyl) (methylvinylsiloxane) copolymer and mixtures thereof.

The silicone-based carriers of the present invention are certain silicone fluids.

The silicone fluid may be either a polyalkyl siloxane, a polyaryl siloxane, a polyalkylaryl siloxane or a polyether siloxane copolymer and is present at a level of from about 0.1% to about 10.0%, preferably from about 0.5% to about 5.0%. Mixtures of these fluids may also be used and are preferred in certain executions. The dispersed silicone particles should also be insoluble in the matrix. This is the meaning of "insoluble" as used hereinbefore and hereinafter.

The polyalkyl siloxane fluids that may be used include, for example, polydimethyl siloxanes with viscosities ranging from about 5 to 600,000 centistokes at 25° C. These siloxanes are available, for example, from the General Electric Company as the Viscasil series and from Dow Corning as the Dow Corning 200 series. The essentially non-volatile polyalkylaryl siloxane fluids that may be used include, for example, polymethylphenylsiloxanes have viscosities of about 0.65 to 30,000 centistokes at 25° C. These siloxanes are available, for example, from the General Electric Company as SF 1075 methyl phenyl fluid or from Dow Corning as 556 Cosmetic Grade Fluid.

Also suitable for use are certain cyclic polydimethylsiloxanes of the formula:

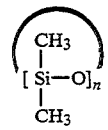

wherein n equals about 3 to about 7.

The viscosity can be measured by means of a glass capillary viscometer as set forth in Dow Corning Corporate Test Method CTM0004, Jul. 29, 1970. Preferably the viscosity ranges from about 350 centistokes to about 100,000 centistokes.

The most preferred silicone component for use herein is a dimethiconol gum having a molecular weight of from about 240,000 to about 260,000 along with a silicone carrier with a viscosity of about 5 cs. An example of this silicone component is Dow Q2-1403 fluid (85% 5cs Dimethyl Fluid/15% Dimethiconol) available from Dow Corning.

Optional Components

Polyglycerylmethacrylate Lubricant

A highly preferred optional component is a water soluble polyglycerylmethacrylate lubricant. This generally should have a viscosity (10% aqueous solution, 20° C., Brookfield RVT) of less than about 4000 cps, preferably less than about 1000 cps and more preferably less than about 500 cps. In additions, the polyglycerylmethacrylate lubricant preferably also has a viscosity (neat) in the range of from about 200 to about 5000 cps (Brookfield RVT, 20° C.), more preferable from about 500 to about 200 cps and especially from about 700 to about 900 cps.

The polyglycerylmethacrylate lubricants which can be used in the compositions of this invention are available under the trademark Lubrajel (RTM) from Guardian Chemical Corporation, 230 Marcus Blvd., Hauppage, N.Y. 11787. In general, Lubrajels can be described as hydrates or clathrates which are formed by the reaction of sodium glycerate with a methacrylic acid polymer. Thereafter, the hydrate or clathrate is stabilized with a small amount of propylene glycol, followed by controlled hydration of the resulting product. Lubrajels are marketed in a number of varying glycerate:polymer ratios and viscosities. Preferred for use herein, however, is so-called Lubrajel Oil, which has a typical viscosity of about 800 cps. Another preferred lubricant is Lubrajel DV which has a typical viscosity of 380,000 cps. Other suitable Lubrajels include Lubrajel TW, Lubrajel CG and Lubrajel MS.

In the present compositions, the polyglycerylmethacrylate is incorporated at a level of from about 0.1% to about 20%, preferably from about 0.2% to about 2%, and more preferably from about 0.3% to about 1% by weight of the composition.

Cationic Surfactant

An optional component of the present compositions is a cationic surfactant which is present at a level of from 0.01% to 5%, more preferably from 0.01% to 2%, and most preferably from 0.01% to 1%. McCutcheon's, *Detergents and Emulsifiers*, North American Edition (1986), published by Allured Publishing Corporation, which is incorporated herein by reference, includes a broad listing of cationic surfactants.

Examples of such useful cationic surfactants include distearyl dimethyl ammonium chloride, dilauryl dimethyl ammonium chloride, N-cetyl pyridinium bromide, alkyl dimethyl ethylbenzyl ammonium cyclohexyl sulfamate, dodecyl dimethyl ethylbenzyl ammonium chloride, alkyl triethanolammonium chloride, dimethyl di(hydrogenated tallow) ammonium chloride, quaternium-15, bis(hydrogenated tallow alkyl)dimethyl methyl sulfates, γ-gluconamidopropyldimethyl-2-hydroxyethyl ammonium chloride, decyl dimethyl octyl ammonium chloride, dimtheyl 2-hydroxyethyl minkamidopropyl ammonium chloride, quaternium-18 Methosulfate, isododecylbenzyl triethanolammonium chloride, cocamidopropyl dimethyl acetamido ammonium chloride, quaternium-45, quaternium-51, quaternium-52, quaternium-53, bis(N-hydroxy-ethyl-2-oleyl imidazolinium chloride) polyethylene glycol 600, lanolin/isosteramidopropyl ethyl dimethyl ammonium ethosulfate, bis[amidopropyl-N,N-dimethyl-N-ethyl) ammonium methosulfate] dimer acid, quaternium-62, quaternium-63, stearamidopropyl dimethyl (myristyl acetate) ammonium chloride, and quaternium-71. These hydrophobic cationic surfactants can be used either singly or as a combination of one or more materials.

The preferred cationic surfactants for use in this invention are the halide salts of N,N,N-trialkylaminoalkylene gluconamides having the formula:

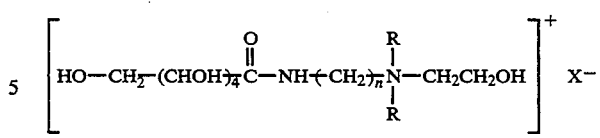

wherein R=alkyl, X=Cl⁻ or Br⁻, and n is an integer from 2 to 4.

Most preferred for use in this invention is γ-gluconamidopropyl dimethyl 2-hydroxyethyl ammonium chloride (CTFA designation Quaternium-22) which has the following structure:

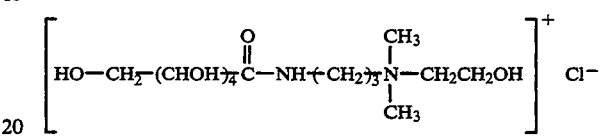

This compound is commercially available as a free-flowing, 60% aqueous solution from Van Dyk, Inc. (Belleville, N.J.) under the trademark Ceraphyl$^R$ 60. U.S. Pat. No. 3,855,290 to Zak et al., issued Dec. 17, 1974; U.S. Pat. No. 3,766,267 to Zak et al., issued Oct. 16, 1973; and U.S. Pat. No. 4,534,964 to Herstein et al., issued Aug.13, 1985, which are all incorporated herein by reference, further describe Quaternium-22 and its use in personal care products.

Additional Water-Soluble Materials

A number of additional water-soluble materials can be added to the composition of the present invention, however. Such materials include the other humectants such as sorbitol, propylene glycol, ethoxylated glucose and hexanetriol; keratolytic agents such as salicylic acid; proteins and polypeptides and derivatives thereof; water-soluble or solubilizable preservatives such as Germall 115, methyl, ethyl, propyl and butyl esters of hydroxybenzoic acid, EDTA, Euxyl(RTM)K400, Bromopol (2-bromo-2-nitropropane-1,3-diol), phenoxypropanol, DMDM Hydantoin/3-Iodo-2-Propynyl Butyl Carbamate (available as Glydant ® and Glydant Plus ®); anti-bacterials such as Irgasan (RTM) and phenoxyethanol (preferably at levels of from 0.5% to about 5%); soluble or colloidally soluble moisturizing agents such as hyaluronic acid, chitosan, and starch-grafted sodium polyacrylates such as Sanwet (RTM) IM-1000, IM-1500 and IM-2500 available from Celanese Superabsorbent Materials Portsmith, Va., USA and described in U.S. Pat. No. 4,076,663; coloring agents; perfumes and perfume solubilizers etc. Water is also present at a level of from about 50% to about 99.3%, preferably from about 80% to about 95% by weight of the compositions herein.

Pharmaceutical Actives

Pharmaceutical actives useful in the present invention include any chemical material or compound suitable for topical administration which induces any desired local or systemic effect. These actives are present at a level from about 0.1% to about 20%. Such substances include, but are not limited to antibiotics, antiviral agents, analgesics, antihistamines, antiinflammatory agents, antipruritics, antipyretics, anesthetic agents, diagnostic agents, hormones, antifungals, antimicrobials, cutaneous growth enhancers, pigment modulators, antiproliferatives, antipsoriatics, retinoids, anti-acne medicaments (e.g. benzoyl peroxide, sulfur, etc.), antineoplastics agents, phototherapeutic agents, keratolytics (e.g. resorcinol, salicylic acid) and sunscreens.

Vitamins

Various vitamins may also be included in the compositions of the present invention. For example, Vitamin A, and derivatives thereof, ascorbic acid, Vitamin B, biotin, panthothenic acid, Vitamin D, and mixtures thereof may be used. Vitamin E, tocopherol acetate and derivatives may also be used.

Other Optional Components

A variety of additional ingredients may be added to the emulsion compositions of the present invention. These additional ingredients include various polymers for aiding the film-forming properties and substantivity of the formulation, preservatives for maintaining the antimicrobial integrity of the compositions, antioxidants, and agents suitable for aesthetic purposes such as fragrances, pigments, and colorings.

The compositions of the invention are in aqueous gel form and are preferably formulated so as to have product viscosity of at least about 4,000 and preferably in the range from about 4,000 to about 300,000 cps, more preferable from about 20,000 to about 200,000 cps and especially from about 80,000 to about 150,000 cps (20° C., neat, Brookfield RVT). Preferably the compositions are visually translucent. The compositions are also substantially free of oil, i.e. contain less than about 1%, and preferably less than about 0.1% of materials which are insoluble or which are not colloidally-soluble in the aqueous gel matrix at 10° C. "Colloidally-soluble" herein refers to particles in the usual colloidal size range, typically from 1 to 1000 nm, especially from 1 to 500 nm. In highly preferred embodiment, the compositions are substantially free of materials which are insoluble or not colloidally soluble in distilled water at 20° C. Such materials include many conventional emollient materials such as hydrocarbon oils and waxes, glyceride esters, alkyl esters, alkenyl esters, fatty alcohols, certain fatty alcohol ethers and fatty acid esters of ethoxylated fatty alcohols, sterols extracted from lanolin, lanolin esters, wax esters, beeswax derivatives, vegetable waxes, phospholipids, sterols and amides. The compositions can, however, contain low levels of insoluble ingredients added, for example for visual effect purposes, e.g. thermochromic liquid crystalline materials such as the microencapsulated cholesteryl esters and chiral nematic (nonsterol) based chemicals such as the (2-methylbutyl) phenyl 4-alkyl(oxy)benzoates available from Hallcrest, Glenview, Ill. 60025, U.S.A.

The compositions of the invention have no need of and are preferably also substantially free of surfactant materials which are conventionally added to cosmetic cream and lotion compositions in order to emulsify a water-insoluble oily phase. Again, "substantially free" means less than about 1%, preferably less than about 0.1% of the indicated materials. Such emulsifiers include ethoxylated fatty acids, ethoxylated esters, phosphated esters, ethoxylated fatty alcohols, polyoxyethylene fatty ether phosphates, fatty acid amides, alkyl lactylates, soaps, alkyl polyglucosides, allyl sucrose esters, allyl polyglycerol esters, etc.

The pH of the compositions is preferably from about 4 to about 9, more preferably from about 4.5 to about 7.

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name.

Example I

A substantially oil-free aqueous skin care gel is made by combining the following ingredients utilizing conventional mixing techniques.

| Ingredient | % W/W |
| --- | --- |
| Glycerine | 3.0 |
| Hexylene Glycol | 1.0 |
| Carbomer 980[1] | 0.5 |
| DL-Panthenol | 0.5 |
| Sodium hydroxide | 0.175 |
| DMDM Hydantoin/3-Iodo-2-Propynyl Butyl Carbamate[2] | 0.1 |
| Disodium EDTA | 0.2 |
| Citric Acid | 0.01 |
| 85% 5cs Dimethyl Fluid/15% Dimethiconol[3] | 3.0 |
| Deionized Water | q.s. |

[1]Carbopol 980 available from B.F. Goodrich
[2]Glydant Plus available from Lonza
[3]Dow Q2-1403 Fluid available from Dow Corning A preservative premix is made by combining Distilled water, Hexylene Glycol, DMDM Hydantoin/3-Iodo-2-Propynyl Butyl Carbamate in a weight/weight (w/w) ratio of 1:1:0.1, respectively. Separately, a 10% w/w solution of DL Panthenol and NaOH is made. Using a Lightnin' Mixer with a 3 blade paddle prop, the Carbomer is dispersd into the water. The Disodium EDTA and Citric Acid are then added. The resultant combination is mixed until the Carbomer is evenly dispersed (approx. 10–15 min for a 1 kg batch). The preservative premix is added under continued mixing. The prop on the Lightnin' Mixer is changed to a high lift prop. While mixing, Glycerin, DL-Panthenol solution, and Q2-1403 fluid are added. NaOH is added to this solution. The solution is mixed for an additional 5–10 minutes.

The compositions display improved skin feel and residue characteristics together with excellent moisturizing, emolliency, rub-in and absorption characteristics.

Example II

A substantially oil-free aqueous skin care gel is made by combining the following ingredients utilizing conventional mixing techniques as described above in Example I.

| Ingredient | % W/W |
| --- | --- |
| Glycerine | 2.0 |
| Hydrogenated Glucose Syrup[1] | 1.0 |
| Butylene Glycol | 1.0 |
| DL-Panthenol | 1.0 |
| Polyglyceryl methacrylate[2] | 15.0 |
| DMDM Hydantoin/3-Iodo-2-Propynyl Butyl Carbamate[3] | 0.1 |
| Disodium EDTA | 0.02 |
| 85% 5cs Dimethyl Fluid/15% Dimethiconol[4] | 3.0 |

| Ingredient | % W/W |
|---|---|
| Deionized Water | q.s. |

[1] Hystar CG available from Lonza
[2] Lubrajel DV available from Freeman, Inc.
[3] Glydant Plus available from Lonza
[4] Dow Q2-1403 Fluid available from Dow Corning The composition displays improved skin feel and residue characteristics together with excellent moisturizing, emolliency, rub-in and absorption characteristics.

Examples III–VI

Substantially oil-free aqueous skin care gels are made by combining the following ingredients utilizing conventional mixing techniques as described above in Example I.

| | % W/W | | | |
|---|---|---|---|---|
| Ingredient | III | IV | V | VI |
| Glycerin | 3.0 | 3.0 | 3.0 | 3.0 |
| Hexylene Glycol | 1.0 | 1.0 | 1.0 | 1.0 |
| Carbomer 980[1] | 0.5 | 0.5 | 0.5 | 0.5 |
| DL-Panthenol | 0.5 | 0.5 | 0.5 | 0.5 |
| Sodium Hydroxide | 0.175 | 0.175 | 0.175 | 0.175 |
| DMDM Hydantoin/3-Iodo-2-Propynyl Butyl Carbamate[2] | 0.1 | 0.1 | 0.1 | 0.1 |
| Disodium EDTA | 0.02 | 0.02 | 0.02 | 0.02 |
| Citric Acid | 0.01 | 0.01 | 0.01 | 0.01 |
| Polyglycerylmethacrylate[3] | 0.5 | — | — | — |
| 85% 5cs Dimethyl Fluid/15% Dimethiconol[4] | 3.0 | 5.0 | — | — |
| 85% 5cs Dimethyl Fluid/15% Dimethiconol Gum[5] | — | — | 3.0 | 5.0 |
| Deionized Water | To 100 | | | |

[1] Carbopol 980 available from B.F. Goodrich
[2] Glydant Plus available from Lonza
[3] Lubrajel Oil available from Freeman, Inc.
[4] Dow Q2-1403 Fluid available from Dow Corning
[5] GE SF 1236 Fluid available from General Electric The compositions display improved skin feel and residue characteristics together with excellent moisturizing, emolliency, rub-in and absorption characteristics.

What is claimed is:

1. A skin care composition in the form of a substantially oil-free aqueous gel comprising:
   (a) from about 0.5% to about 20% by weight of a water-soluble humectant;
   (b) from about 0.1% to about 20% by weight of a hydrophilic gelling agent; and
   (c) from about 1.0% to about 10% by weight of a silicone component consisting essentially of
      i) a silicone gum having a molecular weight of from about 200,000 to about 540,000 selected from the group consisting of dimethiconol, fluorosilicone and dimethicone or mixtures thereof; and
      ii) a silicone-based carrier having a viscosity from about 0.65 cps. to about 100 cps,
      wherein the ratio of i) to ii) is from about 10:90 to about 20:80 and wherein said component has a final viscosity of from about 500 cps. to about 10,000 cps.

2. A composition according to claim 1 wherein the silicone gum component is a dimethiconol of the formula:

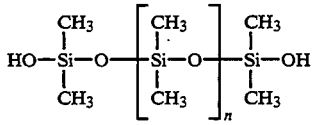

where n is from about 2700 to about 4500, and wherein the molecular weight is from about 200,000 to about 300,000.

3. A composition according to claim 2 wherein the dimethiconol component has a molecular weight of from about 240,000 to about 260,000 and n is from about 3200 to about 4300.

4. A composition according to claim 3 wherein the dimethiconol has a molecular weight of about 250,000 and n is from about 4000 to about 4300.

5. A composition according to claim 4 wherein the silicone-based carrier is an essentially non-volatile silicone fluid selected from the group consisting of polyalkyl siloxanes, polyaryl siloxanes, polyalkylaryl siloxanes, and polyether siloxanes and mixtures thereof.

6. A composition according to claim 5 which further comprises from 0.1% to 10% by weight of a water-soluble polyglycerylmethacrylate lubricant having a viscosity of less than 30,000 cps. as measured in a 10% aqueous solution at 20° C. using a Brookfield RVT; and comprising from 1% to 10% by weight of glycerine.

7. A composition according to claim 6 wherein the polyglycerylmethacrylate lubricant is a hydrate or clathrate formed by the reaction of sodium glycerate with a methacrylic acid polymer.

8. A composition according to claim 7 wherein the hydrophilic gelling agent is present at a level of from about 0.2% to about 2% and has a neutralized viscosity of at least about 10,000 cps.

9. A composition according to claim 8 comprising from 0.3% to 1% by weight of the polyglycerylmethacrylate lubricant.

10. A composition according to claim 9 having a viscosity of from 4000 to 300,000 cps. as measured neat at 20° C. using a Brookfield RVT.

11. A composition according to claim 10 wherein the gelling agent has a neutralized viscosity of at least 50,000 cps. as measured as a 1% aqueous solution at 20° C. using a Brookfield RVT.

12. A composition according to claim 11 wherein the gelling agent is a carboxylic acid copolymer of acrylic acid cross-linked with from 0.75% to 2% of a cross-linking agent selected from polyallyl sucrose and polyallyl pentaerythritol.

13. A composition according to claim 12 wherein the carboxylic acid copolymer is selected from the group consisting of Carbomer 941, Carbomer 951, Carbomer 980, Carbomer 981, Carbomer 1342, and mixtures thereof.

14. A composition according to claim 1 wherein said gel further comprises from about 0.1% to about 20% of a topical pharmaceutical active.

15. A composition according to claim 5 wherein said gel further comprises from about 0.1 to about 2,0% of a topical pharmaceutical active.

16. A composition according to claim 11 wherein said gel further comprises from about 0.1% to about 20% of a topical pharmaceutical active.

* * * * *

UNITED STATES PATENT AND TRADEMARK OFFICE
CERTIFICATE OF CORRECTION

PATENT NO.    :  5,420,118
DATED         :  May 30, 1995
INVENTOR(S)   :  Noelle C. Alban et al.

It is certified that error appears in the above-identified patent and that said Letters Patent is hereby corrected as shown below:

At column 3, line 66 "about 97,9" should read --about 97.9--.

At column 5, lines 27-28 "diethanoiamine" should read --diethanolamine--.

At column 8, lines 10-11 "y-gluconamidopropyl" should read --γ-gluconamidopropyl--.

At column 9, line 24 "have product" should read --have a product--.

At column 10, line 24 "Disodium EDTA    0.2" should read --Disodium EDTA    0.02--.

At column 10, line 36 "DL Panthenol" should read --DL-Panthenol--.

At column 11, line 59 "100 cps," should read --100 cps.,--.

At column 12, line 61 "2,0%" should read --20%--.

Signed and Sealed this

Twenty-third Day of March, 1999

Attest:

Q. TODD DICKINSON

*Attesting Officer*     *Acting Commissioner of Patents and Trademarks*